(12) United States Patent
Lopez-Berestein et al.

(10) Patent No.: US 7,176,302 B2
(45) Date of Patent: Feb. 13, 2007

(54) LIPOSOMAL PHOSPHODIESTER, PHOSPHOROTHIOATE, AND P-ETHOXY OLIGONUCLEOTIDES

(75) Inventors: Gabriel Lopez-Berestein, Houston, TX (US); Ana Maria Tari, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 104 days.

(21) Appl. No.: 10/462,172

(22) Filed: Jun. 16, 2003

(65) Prior Publication Data

US 2004/0005353 A1 Jan. 8, 2004

Related U.S. Application Data

(63) Continuation of application No. 09/536,971, filed on Mar. 28, 2000, now abandoned, which is a continuation of application No. 09/112,869, filed on Jul. 9, 1998, now Pat. No. 6,042,846, which is a continuation of application No. 08/520,385, filed on Aug. 29, 1995, now Pat. No. 5,855,911.

(51) Int. Cl.
C07H 21/04 (2006.01)
A61K 48/00 (2006.01)
C12Q 1/68 (2006.01)

(52) U.S. Cl. .................. 536/24.5; 536/23.1; 514/44; 435/6; 435/325; 435/375

(58) Field of Classification Search ............... 536/23.1; 514/44; 435/6, 325, 375
See application file for complete search history.

(56) References Cited

U.S. PATENT DOCUMENTS

| | | | |
|---|---|---|---|
| 4,229,360 A | 10/1980 | Schneider et al. |
| 4,394,448 A | 7/1983 | Szoka, Jr. et al. |
| 4,469,863 A | 9/1984 | Ts'o et al. |
| 4,480,041 A | 10/1984 | Myles et al. |
| 4,721,612 A | 1/1988 | Janoff et al. |
| 4,835,263 A | 5/1989 | Nguyen et al. |
| 4,837,028 A | 6/1989 | Allen |
| 4,904,582 A | 2/1990 | Tullis |
| 4,920,016 A | 4/1990 | Allen et al. |
| 4,924,624 A | 5/1990 | Suhadolnik et al. |
| 4,950,432 A | 8/1990 | Mehta et al. |
| 5,030,442 A | 7/1991 | Uster et al. |
| 5,049,388 A | 9/1991 | Knight et al. |
| 5,087,617 A | 2/1992 | Smith |
| 5,094,785 A | 3/1992 | Law et al. |
| 5,098,890 A | 3/1992 | Gewirtz et al. |
| 5,100,662 A | 3/1992 | Bolcsak et al. |
| 5,112,962 A | 5/1992 | Letsinger et al. |
| 5,135,917 A | 8/1992 | Burch |
| 5,178,875 A | 1/1993 | Lenk et al. |
| 5,188,897 A | 2/1993 | Suhadolnik et al. |
| 5,202,429 A | 4/1993 | Tsujimoto et al. |
| 5,227,170 A | 7/1993 | Sullivan |
| 5,248,671 A | 9/1993 | Smith |
| 5,264,618 A | 11/1993 | Felgner et al. |
| 5,271,941 A | 12/1993 | Cho-Chung |
| 5,279,833 A | 1/1994 | Rose |
| 5,279,957 A | 1/1994 | Gross |
| 5,320,962 A | 6/1994 | Stiles et al. |
| 5,324,654 A | 6/1994 | Bredesen |
| 5,376,646 A | 12/1994 | Pittrof et al. |
| 5,378,825 A | 1/1995 | Cook et al. |
| 5,417,978 A | 5/1995 | Tari et al. |
| 5,525,719 A | 6/1996 | Srivasta and Raza |
| 5,527,538 A | 6/1996 | Baldeschwieler |
| 5,560,923 A | 10/1996 | Rahman et al. |
| 5,661,018 A | 8/1997 | Ashley et al. |
| 5,665,710 A | 9/1997 | Rahman et al. |
| 5,696,248 A | 12/1997 | Peyman et al. |
| 5,705,385 A | 1/1998 | Bally et al. |
| 5,734,033 A | 3/1998 | Reed |
| 5,750,669 A | 5/1998 | Rosch et al. |
| 5,756,122 A | 5/1998 | Thierry et al. |
| 5,817,811 A | 10/1998 | Breipohl et al. |
| 5,831,048 A | 11/1998 | Schweighoffer et al. |
| 5,831,066 A | 11/1998 | Reed |
| 5,855,911 A | 1/1999 | Lopez-Berestein et al. |
| 5,874,224 A | 2/1999 | Bandman et al. |
| 5,874,553 A | 2/1999 | Peyman et al. |
| 5,891,714 A | 4/1999 | Ashley et al. |
| 5,908,635 A | 6/1999 | Thierry |

(Continued)

FOREIGN PATENT DOCUMENTS

CA 2171589 3/1996

(Continued)

OTHER PUBLICATIONS

Uhlmann et al. Chemical Reviews 1990, v90(4) 545-579.*

(Continued)

Primary Examiner—James Schultz
(74) Attorney, Agent, or Firm—Fulbright & Jaworski LLP (57) ABSTRACT

An improved delivery system for antisense oligonucleotides involves a liposomal composition, comprising a liposome which consists essentially of neutral phospholipids and an antisense oligonucleotide that is entrapped in the liposome and is selected from the group consisting of phosphodiester oligonucleotides, phosphorothioate oligonucleotides, and p-ethoxy oligonucleotides.

6 Claims, 5 Drawing Sheets

U.S. PATENT DOCUMENTS

| | | | |
|---|---|---|---|
| 5,976,567 | A | 11/1999 | Wheeler et al. |
| 6,015,886 | A | 1/2000 | Dale et al. |
| 6,034,235 | A | 3/2000 | Sugiyama et al. |
| 6,040,181 | A | 3/2000 | Reed |
| 6,042,846 | A | 3/2000 | Lopez-Berestein et al. |
| 6,096,720 | A | 8/2000 | Love et al. |
| 6,110,490 | A | 8/2000 | Thierry |
| 6,120,794 | A | 9/2000 | Liu et al. |
| 6,120,798 | A | 9/2000 | Allen et al. |
| 6,126,965 | A | 10/2000 | Kasid et al. |
| 6,136,965 | A | 10/2000 | Bruice et al. |
| 6,211,162 | B1 | 4/2001 | Dale et al. |
| 6,211,349 | B1 | 4/2001 | Dale et al. |
| 6,277,832 | B1 | 8/2001 | Sugiyama et al. |
| 6,277,981 | B1 | 8/2001 | Tu et al. |
| 6,291,668 | B1 | 9/2001 | Ziegler et al. |
| 6,326,487 | B1 | 12/2001 | Peyman et al. |
| 6,414,134 | B1 | 7/2002 | Reed |

FOREIGN PATENT DOCUMENTS

| | | | |
|---|---|---|---|
| DE | | 4110085 | 3/1991 |
| WO | WO 88/04924 | | 7/1988 |
| WO | WO 89/06977 | | 8/1989 |
| WO | WO 90/09180 | | 8/1990 |
| WO | WO 90/10488 | | 9/1990 |
| WO | WO 91/16901 | | 11/1991 |
| WO | WO 92/21330 | | 12/1992 |
| WO | WO 92/22303 | * | 12/1992 |
| WO | WO 93/07883 | | 4/1993 |
| WO | WO 93/11245 | | 6/1993 |
| WO | WO 93/24640 | | 12/1993 |
| WO | WO 94/04545 | | 3/1994 |
| WO | WO 94/05259 | | 3/1994 |
| WO | WO 95/03788 | | 2/1995 |
| WO | WO 96/27663 | | 9/1996 |
| WO | WO 96/40062 | | 12/1996 |
| WO | WO 00/40595 | | 7/2000 |

OTHER PUBLICATIONS

Agrwal, "Antisense oligonucleotides; torwards clinical trials," *TIBTECH*, 14:376-387, 1996.

Agris et al., "Inhibition of vesicular stomatitis virus protein synthesis and infection by sequence-specific oligodeoxyribonucleoside methylposphonates," *Biochemistry*, 25:6268-6275, 1986.

Akhtar et al., "Interactions of antisense DNA oligonucleotide analogs with phospholipid membranes (liposomes)," *Nucleic Acids Research*, 19(20): 5551-5559, 1991.

Akhtar et al., "Liposome delivery of antisense methylphosphonate and phosphorothioate oligonucleotides: A study with MLV, FATMLV, and LUV liposomes," *Proceed Intern. Symp. Control. Rel. Bioact. Mater.*, 19:345-346, 1992.

Akhtar et al. "Release of antisense oligdeoxynucleotide analogues from liposomes: implications for cellular transport and drug delivery," 128th Meeting of British Pharmaceutical Conference 1991, United Kingdom, Sep. 10-13, 1991, *J. Pharm. Pharmacol.*, 43 (Suppl.):Abstract 24P, 1991.

Arad et al., "Use of reconstituted sendai virus envelopes for fusion-mediated microinjection of double-stranded RNA: Inhibition of protein synthesis in interferon-treated cells," *Biochimica et Biophysica Acta*, 859:88-94, 1986.

Bakhshi et al., "Cloning the Chromosomal Breakpoint of t(14;18) Human Lymphomas: Clustering around $J_H$ on Chromosome 14 and near a Transcriptional Unit on 18," *Cell*, 41:899, 1985.

Bennett et al., "Cationic lipids enhance cellular uptake and activity of phosphorothioate antisense oligonucleotides," *Molecular Pharmacology*, 41(6):1023-1033, 1992.

Boiziau et al., "Modified oligonucleotides in rabbit reticulocytes: uptake, stability and antisense properties," Biochimie, 73:1403-1408, 1991.

Branch, A., "A good antisense molecule is hard to find," *TIBS*, 23:45-49, 1998.

Budker et al., "Cell membranes as barriers for antisense construction," *Antisense Research and Development*, 2:177-184, 1992.

Capaccioli et al., "Cationic lipids improve antisense oligonucleotide uptake and prevent degradation in cultured cells and in human serum," *Biochemical and Biophysical Research Communications*, 197(2):818-825, 1993.

Citro et al., "Chemical modification of ligands for cell receptors to introduce foreign compounds into the cells," *Colon & Rectum*, 37(2):S127-S132, 1994.

Clarenc et al., "Delivery of antisense oligonucleotides by poly(l-lysine) conjugation and liposome encapsulation," *Anti-Cancer Drug Design*, 8:81-94, 1993.

Cotter et al., "Antisense oligonucleotides supress B-cell lymphoma growth in a SCID-hu mouse model." *Oncogene*, 9:3-49-3055, 1994.

Gerwirtz et al., "Facilitating oligonucleotide delivery: helping antisense delivery on its promise," *Proc. Natl. Acad. Sci U.S.A.*, 93: 3161-3163, 1996.

Gura, "Antisense has growing pains," *Science*, 270:575-577, 1995.

Juliano et al., "Liposomes as a drug delivery system for antisense oligonucleotides," *Antisense Research and Development* 2:165-176, 1992.

Keller et al., "Synthesis and hybridization properties of oligonucleotides containing 2'-O-modified ribonucleotides," *Nucleic Acids Research*, 21(19):4499-4505, 1993.

Krieg et al., "Modification of antisense phosphodiester oligodeoxynucleotides by a 5' cholesteryl moiety increases cellular association and improves efficacy," *Proc. Natl. Acad. Sci., USA*, 90:1048-1052, 1993.

Kramer et al., "Self-specific T lymphocyte lines as vehicles for gene therapy: myelin specific T cells carrying exogenous nerve growth factor gene (abstract)," *J. Cell. Biochem.*, Suppl. o (17 Part E):215, 1993.

Leonetti et al., "Antibody-targeted liposomes containing oligodeoxyribonucleotides complementary to viral RNA selectively inhibit viral replication," *Proc. Natl. Acad. Sci. USA*, 87:2448-2451, 1990.

Loke et al., "Delivery of c-*myc* antisense oligodeoxynucleotides to hematopoietic cells in culture by liposome fusion: Specific reduction in c-*myc* protein expression corelates with inhibition of cell growth and DNA synthesis," *Clinical Research*, AFCR Immunology Abstract, 36(3):443A, 1988.

Loke et al., "Delivery of c-*myc* antisense phosphorothioate oligodeoxynucleotides to hematopoietic cells in culture by liposome fusion: specific reduction in c-*myc* protein expression correlates with inhibition of cell growth and DNA synthesis," *Current Topics in Microbiology and Immunology, Mechanisms in B-Cell Neoplasia*, 141:282-289, 1988.

Martiat et al., "Retrovirally transduced antisense sequences stably suppress $P210^{BCR-ABL}$ expression and inhibit the proliferation of BCR/ABL-containing cell lines," *Blood*, 81(2):502-509, 1993.

Miller et al., "Gene Transfer and antisense nucleic acid techniques," *Parasitology Today*, 10(3):92-97, 1994.

Miller, "Oligonucleoside methylphosphonates as antisense reagents," *Bio/Technology*, 9:358-362, Apr. 1991.

Moody et al., "Regiospecific inhibition of DNA duplication by antisense phosphate-methylated oligodeoxynucleotides," *Nucleic Acids Research*, 17(12):4769-4782, 1989. (Abstract).

Pihl-Carey et al., "Isis to restructure as Crohn's disease drug fails in phase III," *Daily Biotech. Newspaper*, 10:1-2, 1999.

Renneisen et al., "Inhibition of expression of human immunodeficiency virus-1 *in vitro* by antibody-targeted liposomes containing antisense RNA to the *env* region," *The Journal of Biological Chemistry*, 265(27):16337-16342, 1990.

Rojanasakul, "Antisense oligonucleotide therapeutics: drug delivery and targeting," *Advanced Drug Delivery Reviews*, 18:115-131, 1996.

Ropert et al., "Inhibition of the friend retrovirus by antisense oligonucleotdies encapsulated in liposomes: mechanism action," *Pharmaceutical Research*, 10(10):1427-1433, 1993.

Shea et al., "Synthesis, hybridization properties and antiviral activity of lipid-oligodeoxynucleotide conjugates," *Nucleic Acids Research*, 18(13):3777-3783, 1990.

Skorski et al., "Gene-targeted specific inhibition of chronic myeloid leukemia cell growth by BCR-ABL antisense oligodeoxynucleotides," *Folia Histochemica et Cytobiologica*, 29(3):85-90, 1991.

Stein et al., "Oligodeoxynucleotides as inhibitors of gene expression: A review," *Cancer Research*, 48(10):2635-2944, 1988.

Stein, C.A. et al, "Antisense oligonucleotides as therapeutic agents-is the bullet really magical?," *Science*, 261:1004-1012, Aug. 1993.

Stull et al., "Antigene, ribozyme and aptamer nucleic acid drugs: progress and prospects, pharmaceutical research," 12(4):465-483, 1995.

Szczylik et al., Selective inhibition of leukemia cell proliferation by BCR-ABL antisense oligodeoxynucleotides,,Science, 253:562-565, 1991.

Taj et al., "Inhibition of $P210^{BCR/ABL}$ expression in K562 cells by electroporation with an Antisense oligonucleotide," *Leukemia and Lymphoma*, 3:201-208, 1990.

Tari et al., "Liposomal delivery of methylphosphonate antisense oligodeoxynucleotides in chronic myelogenous leukemia," *Blood*, 84(2): 601-607, 1994.

Thierry et al., "Liposomal delivery as a new approach to transport antisense oligonucleotides," *Gene Regulation, Biology of Antisense RNA and DNA*, 1: 147-161, 1992.

Theirry et al., "Intracellular availability of unmodified, phosphorothioated and liposomally encapsulated oligodeoxynucleotides for antisense activity," *Nucleic Acids Research*, 20(21):5691-5698, 1992.

Thierry et al., "Overcoming multidrug resistance in human tumor cells using free and liposomally encapsulated antisense oligodeoxynucleotides," *Biochemical and Biophysical Research Communications*, 190(3):952-960, 1993.

Thierry et al., "Modulation of multidrug resistance by antisense oligodeoxynucleotides encapsulated by liposomes", *Proceedings of the American Association for Cancer Research, Preclinical Pharmacology/Experimental Therapeutics*, 32:433, Abstract 2578, 1991.

Thompson, C. B., "Apoptosis in the Pathogenesis and Treatment of Disease," *Science*, 267:1456-1462, 1995.

Tidd et al., "Evaluation of N-*ras* oncogene anti-sense, sense and nonsense sequence methylphosphonate oligonucleotide analogues," *Anti-Cancer Drug Design*, 3:117-127, 1988.

Tidd et al., "Partial protection of oncogene, anti-sense oligodeoxynucleotides against serum nuclease degradation using terminal methylphosphonate groups," *Be. J. Cancer*, 60:343-350, 1989.

Tormo et al., "Antitumor activity of liposomal-bcl-2-antisense oligonucleotides in follicular lymphoma (abstract)," *Proc. Am. Assoc. Cancer. Res.*, 37:1190, 1996.

Tsujimoto et al., "The t(14;18) chromosome translocation involved in B-cell neoplasms result from mistakes in VDJ joining," *Science*, 229:1390, 1985.

Tsuchida et al., "Iron-ligand bonding properties of synthetic iron-porphyrin complexes with oxygen transporting ability in aqueous media," *J. Chem. Soc. Dalton Transactions*, 10:2455-2458, 1987.

Uhlmann et al., "Antisense oligonucleotides: a new therapeutic principal," *Chemical Reviews*, 90(4):543-584, 1990.

Vasanthakumar et al., "Modulation of drug resistance in a daunorubicin resistant subline with oligonucleoside methylphosphonates," *Cancer Communications*, 1(4):225-232, 1989.

Wagner, "Gene inhibition using antisense oligodeoxynucleotides," *Nature*, 372:333-335, 1994.

Webb et al., "Extrathymic Tolerance of Mature T Cells: Clonal Elimination as a Consequence of Immunity," *Cell*, 63:1249, 1990.

Weis, "Upping the antisense ante scientists bet on profits from reverse genetics," *Science News*, 139:108-109, 1991.

Wickstrom, "Antisense DNA therapeutics neutral analogs and their stereochemistry," *Raven Press Ser. Mol. Cell. Biol.*, 1:119-132, 1992.

Williams, G.T., "Programmed Cell Death: Apoptosis and Oncogenesis," *Cell*, 65:1097-1098, 1991.

Yeoman et al.,"Lipofectin enhances cellular uptake of antisense DNA while inhibiting tumor cell growth," *Antisense Research and Development*, 2:51-59, 1992.

Zhang et al., "Gene therapy for the peripheral nervous system rat neuritogenic T cell line carry mouse nerve growth factor gene (abstract)," *J. Cell. Biochem.*, Suppl. 0 (17 Part E):SZ-116, 1993.

International Search Report from the Patent Corporation Treaty, Mar. 14, 1997.

Miller et al., "Synthesis of oligodeoxyribonucleotide ethyl phosphotriesters and their specific complex formation with transfer ribonucleic acid," *Biochemistry*, 13(24):4887-4896, 1974.

* cited by examiner

LIPOSOMAL PHOSPHODIESTER, PHOSPHOROTHIOATE, AND P-ETHOXY OLIGONUCLEOTIDES

This is a continuation of application Ser. No. 09/536,971, filed Mar. 28, 2000 (now abandoned), which is a division of application Ser. No. 09/112,869, filed Jul. 9, 1998, now issued as U.S. Pat. No. 6,042,846, which is a continuation of Ser. No. 08/520,385, filed Aug. 29, 1995, now issued as U.S. Pat. No. 5,855,911.

BACKGROUND OF THE INVENTION

The present invention relates to liposomal formulations of certain antisense oligonucleotides, specifically liposomal phosphodiester, phosphorothioate, and p-ethoxy oligonucleotides. The invention also relates to methods of making such formulations and methods of using such formulations in medical therapy.

Antisense oligonucleotides (oligos), complementary to specific regions of the target mRNA, have been used to inhibit the expression of endogenous genes. When the antisense oligonucleotides bind to the target mRNA, a DNA-RNA hybrid is formed. This hybrid formation inhibits the translation of the mRNA and, thus, the gene's expression of the protein. If the protein is essential for the survival of the cell, the inhibition of its expression may lead to cell death. Therefore, antisense oligonucleotides can be useful tools in anticancer and antiviral therapies.

The main obstacles in using antisense oligonucleotides to inhibit gene expression are cellular instability, low cellular uptake, and poor intracellular delivery. Natural phosphodiesters are not resistant to nuclease hydrolysis; thus high concentrations of antisense oligonucleotides are needed before any inhibitory effect is observed. Modified phosphodiester analogs, such as phosphorothioates, have been made to overcome this nuclease hydrolysis problem, but they have not provided a completely satisfactory solution to the problem.

The cellular uptake of antisense oligonucleotides is low. To solve this problem, physical techniques such as calcium-phosphate precipitation, DEAE-dextran mediation, or electroporation have been used to increase the cellular uptake of oligonucleotides. These techniques are difficult to reproduce and are inapplicable in vivo. Cationic lipids, such as Lipofectin, have also been used to deliver phosphodiester or phosphorothioate oligonucleotides. An electrostatic interaction is formed between the cationic lipids and the negatively charged phosphodiester or phosphorothioate oligonucleotides, which results in a complex that is then taken up by the target cells. Since these cationic lipids do not protect the oligonucleotides from nuclease digestion, they are only useful in delivering the nuclease-resistant phosphorothioates, but not the nuclease-cleavable phosphodiesters.

Another modified phosphodiester (PD) analog that has been prepared is p-ethoxy (pE) oligos. The modifications of pE oligos are made in the phosphate backbone so that the modification will not interfere with the binding of these oligos to the target mRNA. pE oligos are made by adding an ethyl group to the nonbridging oxygen atom of the phosphate backbone, thus rendering these oligos uncharged compounds. In spite of their resistance to nucleases, the cellular uptake and intracellular delivery of pE oligos are still poor because upon internalization, these oligos remain sequestered inside the endosomal/lysosomal vacuoles, impeding their access to the target mRNA.

There is a need for improved antisense compositions for use in treatment of disease, and also a need for processes for making such improved compositions.

SUMMARY OF THE INVENTION

One embodiment of the present invention is a liposomal composition of antisense oligonucleotides. The composition includes (a) a liposome which consists essentially of neutral phospholipids, and (b) an antisense oligonucleotide that is entrapped in the liposome and is selected from the group consisting of phosphodiester oligonucleotides, phosphorothioate oligonucleotides, and p-ethoxy oligonucleotides. The phospholipids are preferably phosphatidylcholines. An especially preferred phospholipid is dioleoylphosphatidyl choline. When the antisense oligonucleotide is a phosphodiester oligonucleotide, the preferred molar ratio of phospholipid to oligo is less than about 3,000:1. When the antisense oligonucleotide is a phosphorothioate oligonucleotide, the preferred molar ratio of phospholipid to oligo is between about 10:1 and about 50:1. When the antisense oligonucleotide is a p-ethoxy oligonucleotide, the preferred molar ratio of phospholipid to oligo is between about 5:1 and about 100:1.

Another embodiment of the present invention is a method of inhibiting the growth of tumor cells in mammals. The method comprises the step of administering to a mammalian subject having a tumor an amount of the above-described composition that is effective to inhibit the growth of tumor cells.

Another embodiment of the present invention is a method of preparing the liposomal composition of antisense oligonucleotides. The method comprises the steps of (a) hydrating a lyophilized composition that consists essentially of neutral phospholipids and an antisense oligonucleotide that is selected from the group consisting of phosphodiester oligonucleotides, phosphorothioate oligonucleotides, and p-ethoxy oligonucleotides, thereby forming an aqueous suspension which includes free oligonucleotide and liposomes entrapping oligonucleotide; and (b) separating the free oligonucleotide from the liposomes by dialysis. In a preferred embodiment, the aqueous suspension is sonicated before dialysis.

The compositions of the present invention constitute an improved delivery system for antisense oligos, such as those used in anti-cancer therapy. In addition to minimizing nuclease hydrolysis of the oligos, the liposomal compositions of the present invention result in increased cellular uptake and intracellular delivery of the antisense oligos, as compared to prior art compositions. Therefore, when such compositions are used to deliver oligos that inhibit the expression of a gene found in cancerous cells but not in normal cells, the therapeutic results are enhanced. Cancers which may be treated in accordance with the present invention would be numerous, with leukemias being one prominent example.

The formulations of the present invention also enhance the incorporation of oligos in the liposomes, as compared to prior art liposomal formulations.

DETAILED DESCRIPTION OF SPECIFIC EMBODIMENTS

"Liposomes" is used in this patent to mean lipid-containing vesicles having a lipid bilayer, as well as other lipid carrier particles which can entrap antisense oligonucleotides. The liposomes can be made of one or more phospholipids, as long as the lipid material is substantially uncharged. It is important that the composition be substantially free of anionic and cationic phospholipids and cholesterol. Suitable phospholipids include phosphatidyl cholines and others that are well known to persons that are skilled in this field. The liposomes can be, for example, unilamellar, multilamellar, or have an undefined lamellar structure. A pharmaceutical composition comprising the liposomes will usually include a sterile, pharmaceutically acceptable carrier or diluent, such as water or saline solution.

"Entrap," "encapsulate," and "incorporate" are used in this patent to mean that the oligo is enclosed within at least some portion of the inner aqueous space (including the interlamellar regions of the bilayer) of the liposome.

A composition of the present invention is preferably administered to a patient parenterally, for example by intravenous, intraarterial, intramuscular, intralymphatic, intraperitoneal, subcutaneous, intrapleural, or intrathecal injection, or may be used in ex vivo bone marrow purging. Preferred dosages are between 5–25 mg/kg. The administration is preferably repeated on a timed schedule until the cancer disappears or regresses, and may be in conjunction with other forms of therapy.

The making and use of the present invention is further illustrated by the following examples.

EXAMPLE 1

Materials

Phosphodiester and phosphorothioate oligonucleotides were provided by Genta Incorporated. Phospholipids were purchased from Avanti Polar Lipids.

Oligonucleotide Labeling

Phosphodiesters were labeled at 37° C. for 8 h with [$^{32}$Pγ]ATP at the 5' end by T4 kinase. The labeled oligonucleotide was precipitated with ethanol at −20° C. overnight. After washing with 70% ethanol three times, phosphodiester oligonucleotides were twice filtered with a Microcon-3 filter to separate the labeled oligonucleotides from free [$^{32}$Pγ]ATP.

Phosphorothioates, labeled with $^{35}$S, were provided by Genta Incorporated.

Liposomal-Phosphodiester Preparation

Phosphodiester oligonucleotides dissolved in distilled water were mixed with phospholipids in the presence of excess t-butanol so that the final volume of t-butanol in the mixture was 80–90%. Trace amounts of [$^{3}$H]cholestanyl ether and [$^{32}$P]phosphodiester were also added to the mixture as lipid and oligonucleotide markers, respectively. The mixture was vortexed before being frozen in an acetone/dry ice bath. The frozen mixture was lyophilized and hydrated with hepes buffered saline (1 mM Hepes and 10 mM NaCl) overnight. Liposomes were twice sonicated for 10 min in a bath type sonicator.

Liposomal-Phosphorothioate Preparation

Liposomal-phosphorothioates were prepared similarly to that described for liposomal-phosphodiesters, except phosphorothioates, instead of phosphodiesters, were used. Also, [$^{35}$S]phosphorothioates, instead of [$^{32}$P]phosphodiesters, were used as the oligonucleotide marker.

Separation of Free Oligonucleotides from Those Incorporated in Liposomes

The separation of free phosphodiester or phosphorothioate oligonucleotides from those incorporated in liposomes was done by dialyzing the mixture against an excess 2500-fold volume of RPMI medium at room temperature overnight. Aliquots of the preparation were taken before and after dialysis for liquid scintillation counting to assess the incorporation of phosphodiester or phosphorothioate oligonucleotides in liposomes.

Development of Liposomal-Phosphodiesters

Dioleoylphosphatidylcholine (DOPC) lipids were chosen for the phosphodiester (PD) incorporation because they are neutral while PD is negatively charged. By using this lipid, electrostatic repulsion (which can lower incorporation) may be reduced. Positively charged lipids were not used because they may induce non-specific cellular toxicity. The initial attempts of incorporating PD oligonucleotides into liposomes were done by using freeze-and-thaw, and dehydration-rehydration methods.

(A) Freeze-and-Thaw (FT) Method.

[$^{3}$H]labeled DOPC lipids were evaporated from their organic solvent under nitrogen gas to form a lipid film. After vacuum desiccation, the lipid film was hydrated with hepes buffered saline (1 mM Hepes, 10 mM NaCl, pH 8.0) and sonicated in a bath type sonicator. These pre-formed liposomes were then mixed with [$^{32}$P]labeled PD oligonucleotides at a 100 or 1000 to 1 molar ratio. The whole mixture was frozen in an acetone/dry ice bath for 5–10 minutes and thawed at room temperature for 25–30 minutes. This process was repeated three times before the sample was loaded on a BioGel A0.5M column for separation of free PD oligonucleotides from liposomal-PD. Aliquots were taken before and after the freeze-thaw procedure and were sent to liquid scintillation counting to determine the incorporation of phosphodiesters into liposomes.

Incorporation was determined by
 [$^{32}$P]PD/μmole [$^{3}$H]DOPC after freeze-thaw X100%
 [$^{32}$p]PD/μmole [$^{3}$H]DOPC before freeze-thaw There was no incorporation (Table 1).

(B) Dehydration-Rehydration (DR) Method

[$^3$H]labeled DOPC was evaporated from the organic solvent under nitrogen gas to form a lipid film. After vacuum desiccation, the lipid film was hydrated with hepes buffered saline and sonicated in a bath type sonicator. These pre-formed liposomes were then frozen in an acetone-dry ice bath and lyophilized. The dried lipids were then rehydrated with distilled water containing [$^{32}$P]phosphodiester oligonucleotides. The molar ratio of DOPC to PD was either 100/1 or 1000/1. The mixture was loaded on a BioGel A0.5M column for separation of free PD oligonucleotides from liposomal-PD. Aliquots were taken before and after column loading and were sent to liquid scintillation counting. The incorporation was <5% (Table 1).

TABLE 1

Comparison of Freeze-thaw (FT) and Dehydration-rehydration (DR) methods on the incorporation of PD into DOPC liposomes.

| Molar ratio | Methods | % incorporation |
|---|---|---|
| 100/1 | FT | 0 |
| | DR | 2.0 |
| 1000/1 | FT | 0 |
| | DR | 4.6 |

With 500/1 and 5000/1 molar ratios of DOPC to PD, 0 and 5.2% incorporation were obtained, respectively.

It was then found that by adding t-butanol to the mixture before freezing and lyophilization, incorporation was raised to 11.9%. Also, by reducing the volume of distilled water added during the rehydration process from 200 to 50 µl, 11.9 versus 1.8% incorporation was obtained with 1000/1 molar ratio. Effect of molar ratio on the incorporation was again measured with these improved conditions (Table 2).

TABLE 2

Effect of lipid to oligonucleotides molar ratio on the incorporation of PD into liposomes.

| Molar ratio | % incorporation |
|---|---|
| 1000/1 | 11.9 |
| 2000/1 | 17.0 |
| 3000/1 | 13.4 |
| 4000/1 | 5.5 |
| 5000/1 | 9.2 |

PD dissolved in distilled water was mixed with DOPC in the presence of excess t-butanol so that the final volume of t-butanol in the mixture was 80–90% before of excess in an acetone/dry ice bath and lyophilized. This was to avoid the step of preparing pre-formed liposomes. With this procedure, similar level of incorporation (16.2%) was obtained at the 2000/1 molar ratio.

It was decided to change the method of separation of free PD from liposomal-PD because the recovery of lipids and PD were <50%. Two other separation methods were used: Microcon-10 filters and dialysis (Table 3).

TABLE 3

Comparison of different methods of separating free PD from PD incorporated in liposomes.[a]

| Method | % Incorporation | % Lipid and PD recovery |
|---|---|---|
| Column | 11.9 | 40–50 |
| Filter | 44.7 | 60–70 |
| Dialysis | 76.7 | >90 |

[a]DOPC was used to incorporate PD oligonucleotides at a 1000/1 molar ratio.

When the liposomal mixture was sonicated for 10 min before the dialysis separation process, similar level of incorporation was obtained. Another lipid, dimyristoyl phosphatidylcholine, was also used for PD incorporation. There was >85% incorporation.

Development of Liposomal-Phosphorothioates

Similar incorporation protocol was used with phosphorothioates (PT) since PT and PD are structural analogs. Various molar ratios of DOPC to PT were used (Table 4). The effect of sonication of the liposomal mixture (before dialysis) was also studied.

TABLE 4

Effect of lipid to oligonucleotide molar ratios on the incorporation of PT into liposomes.

| Molar ratio | % incorporation without sonication | with sonication |
|---|---|---|
| 10/1 | >90 | >90 |
| 50/1 | >90 | >90 |
| 100/1 | 45.8 | 55.5 |
| 200/1 | 44.1 | 49.1 |
| 500/1 | 27.8 | 47.0 |
| 1000/1 | 25.1 | 42.1 |

EXAMPLE 2

Incorporation of P-ethoxy Oligos Into Liposomes pE oligos were purchased from Oligos Therapeutics (Willsonville, Oreg.). Phospholipids were purchased from Avanti Polar Lipids, Inc. (Alabaster, Ala.).

(a) Oligo Labeling pE oligos were labeled at 37° C. for 24 h with [$^{32}$Pγ]ATP at the 5' end by T4 polynucleotide kinase, and then precipitated with ethanol at −20° C. overnight. They were then washed with 70% ethanol three times to separate the labeled oligo from free [$^{32}$Pγ]ATP.

(b) Liposome Preparation pE oligos dissolved in distilled H$_2$O were mixed with phospholipids at various molar ratios in the presence of excess t-butanol so that the final volume of t-butanol in the mixture was at least 95%. Trace amounts of [$^3$H]cholestanyl ether and [$^{32}$P]pEs were also added to the mixture as lipid and oligo markers, respectively. The mixture was vortexed, frozen in an acetone/dry ice bath and then lyophilized. The lyophilized preparation was hydrated with Hepes buffered saline (1 mM Hepes and 10 mM NaCl) at a final oligo concentration of 10–100 µM. The liposomal-p-ethox oligos were sonicated for 10–20 min in a bath type sonicator.

(c) Separation of Free pE Oligos from those Incorporated in Liposomes

The separation of free pE oligos from those incorporated in liposomes was done by dialyzing (MW cutoff=12–14, 000) against 1000-fold excess of Hepes buffered saline at room temperature overnight. Aliquots of liposomal-pE oligos were taken before and after dialysis for liquid scintillation counting to access the incorporation of pE oligos in liposomes.

(d) Incorporation Efficiency

The lipid phosphatidylcholine (PC) was chosen for the incorporation of pE oligos because both PC and pE oligos are neutral molecules so they should be compatible. Among all the different PCS, dioleoyl PC (DOPC) was chosen because it has a chain-melting phase transition temperature at −15 to −20° C. Thus, at room temperature, DOPC is in the liquid crystalline phase which is the ideal phase to prepare liposomes.

To incorporate pE oligos into liposomes, different molar ratios of pE oligos were mixed with DOPC together in the presence of excess of t-butanol. Trace amounts of radio labeled pE oligos and DOPC were included in the mixture. The DOPC/pE oligos mixtures were frozen in a dry ice/acetone bath before being lyophilized. The lyophilized DOPC/pE oligo powder was then hydrated with Hepes buffered saline so that the final oligo concentration was 10 µM. pE oligos were successfully incorporated into DOPC liposomes, ranging between 28 to 83% efficiency (Table 5). The incorporation efficiency was dependent on the molar ratios of DOPC to pE oligos: 10>100>5>1000:1.

TABLE 5

Effect of molar ratio of DOPC to pE oligos on the incorporation of pE oligos

| Molar ratio of DOPC:pE oligos | Incorporation efficiency (%)[a] |
| --- | --- |
| 5:1 | 45 |
| 10:1 | 83 |
| 100:1 | 71 |
| 1000:1 | 28 |

[a]The incorporation efficiency values were obtained from three separate experiments.

Delivery of pE Oligos to Leukemic Cells

After achieving a high incorporation efficiency (>80%) of pE oligos into liposomes, we then proceeded to test whether these liposomal-pE oligos can reach the cytoplasm in which the mRNA is located. We had purchased a 16-mer pE oligo labeled with rhodamine at the 5' end so that we could visualize the localization of the pE oligos by fluorescent microscopy.

(a) Incubation of pE Oligos with Leukemic Cells

Figure 1A:
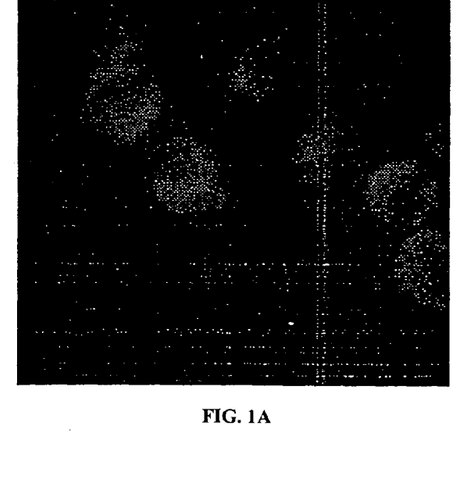
FIGS. 1A and 1B are photographs showing the uptake of (A) free and (B) liposomal pE oligos by ALL-1 cells.
Figure 1B:
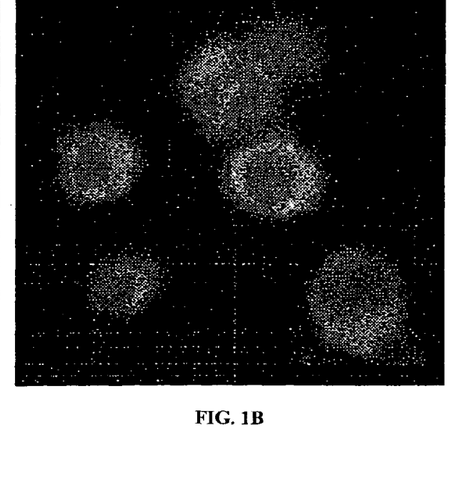

ALL-1 cells, which are human acute lymphocytic leukemic cells, were used. Fifty thousand ALL-1 cells/well were plated in a 24-well plate in 0.3 mL of medium. After 2 h of plating, final concentrations of 16 µM of liposomal or free pE oligos conjugated with rhodamine were added to ALL-1 cells. After 24 h of incubation, the cells were thrice washed with phosphate buffered saline before being viewed under a confocal laser scanning microscope. See FIG. 1 (Uptake of (A) free or (B) liposomal-pE oligos by ALL-1 cells).

Our data indicates that when incorporated into liposomes, higher amounts of pE oligos were taken up by the ALL-1 cells. The liposomes were able to deliver the pE oligos to the cytoplasm.

Growth Inhibition of Liposomal-pE Oligos on Leukemic Cells

We then proceeded to test whether liposomal-pE oligos can specifically inhibit the growth of leukemic cells. We have used three different kinds of human leukemic cell lines: ALL-1 (acute lymphocytic leukemia), BV173 and K562 (both are chronic myelogenous leukemia). All three cell lines contain the rearranged Philadelphia (Ph) chromosome which arises from a reciprocal translocation of chromosomes 9 and 22. This translocation results in the relocation of the c-Abl protooncogene from chromosome 9 onto the 3' end of the breakpoint cluster region (Bcr) of chromosome 22, thus producing a hybrid Bcr-Abl gene. The breakpoint junctions where the Bcr and the Abl genes fuse are different in the three cell lines. In ALL-1 cells, the breakpoint junction is Bcr exon 1/Abl exon 2. In BV173 cells, the breakpoint junction is Bcr exon 2/Abl exon 2. In K562 cells, the breakpoint junction is Bcr exon 3/Abl exon 2. All these hybrid genes produce a novel Bcr-Abl fusion protein, which has enhanced tyrosine kinase activity that has been linked to the pathogenesis of the leukemias. Thus, inhibition of the production of the Bcr-Abl protein may lead to leukemic cell growth inhibition and even cell death. To specifically inhibit the production of the Bcr-Abl protein, we have decided to target the antisense sequences against the breakpoint junctions of the Bcr-Abl mRNA which is only found in Ph chromosome-positive leukemic cells, but not normal cells. This way, we hope to induce minimal non-specific toxic side effects as only leukemic, not normal, cell growth will be affected.

(a) Sequences of the pE antisense oligos (written from 5' to 3' end) antisense against Bcr exon 1/Abl exon 2 (B1/A2) found in ALL-1 cells GAAGGGCTTCTGCGTC (SEQ ID NO:1) antisense against Bcr exon 2/Abl exon 2 (B2/A2) found in BV173 cells CTGAAGGGCTTCTTCC (SEQ ID NO:2) antisense against Bcr exon 3/Abl exon 2 (B3/A2) found in K562 cells

GGGCTTTTGAACTCTGCT (SEQ ID NO:3)

(b) Delivery of Liposomal-pE Oligos to Leukemic Cells

Ten thousand ALL-1 or BV173 cells or five thousand K562 cells were plated per well in a 96-well plate in 100 µL of RPMI medium containing 10% fetal calf serum. After 2 h of plating, final concentrations of 0–10 µM of liposomal-pE oligos were added to leukemic cells. The cells were incubated with liposomal-pE oligos for 5 days. HL60 cells, a human promyelocytic cell line which does not have the Philadelphia chromosome, were used as control cells. They were plated under the same conditions at ten thousand cells/well.

(c) Determination of the Viability of the Leukemic Cells

At the end of the incubation, 100 µL of medium were added to each well which makes the final volume of each well to be 200 µL. Then 50 µL of cells were aliquoted and added to 96-well plates containing 130 µL of medium and 20 µL of alamarBlue dye. The cells will be incubated for 4–8 more hours at 37° C. before being read directly on a microplate reader (Molecular Devices, Menlo Park, Calif.) at 570 and 595 nm. The alamarBlue dye incorporates an oxidation-reduction indicator that changes color in response to chemical reduction of growth medium resulting from cell growth. The difference in absorbance between 570 and 595 nm will be taken as the overall absorbance value of the leukemic cells. The viabilities of leukemic cells treated with liposomal-pE oligos will be compared with those of the control untreated cells.

Figure 2A:
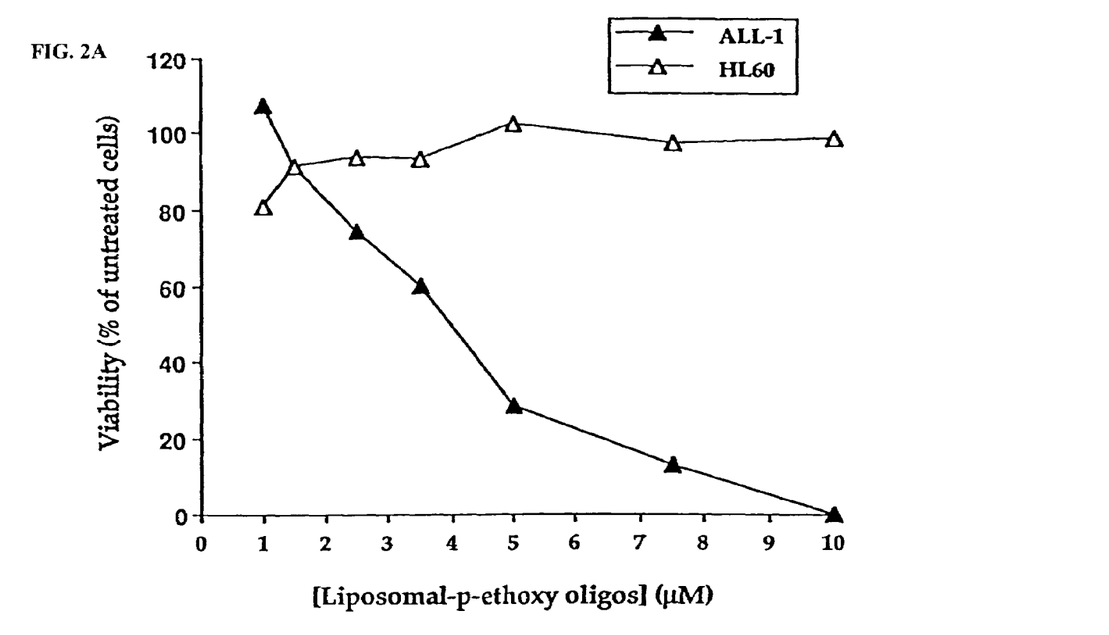
FIG. 2A shows the extent of growth inhibition that resulted when ALL-1 and HL60 cells were incubated with liposomal-pE antisense oligos targeted against the B1/A2 breakpoint junction of Bcr-Abl mRNA.
Figure 3A:
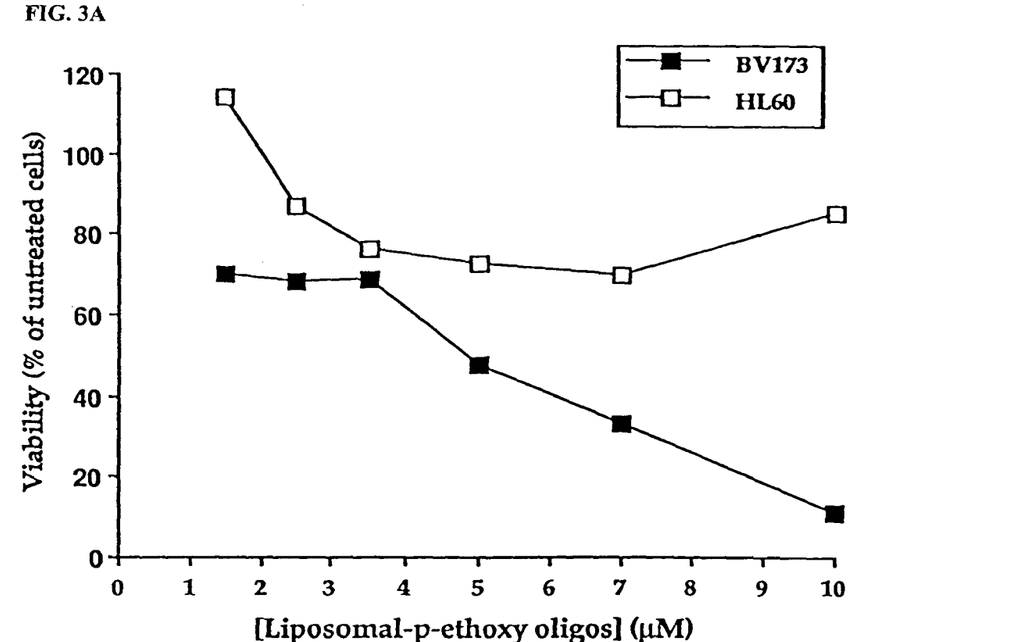
FIG. 3A shows the extent of growth inhibition that resulted when BV173 and HL60 cells were incubated with liposomal-pE antisense oligos targeting against the B2/A2 breakpoint junction of Bcr-Abl mRNA.
Figure 4A:
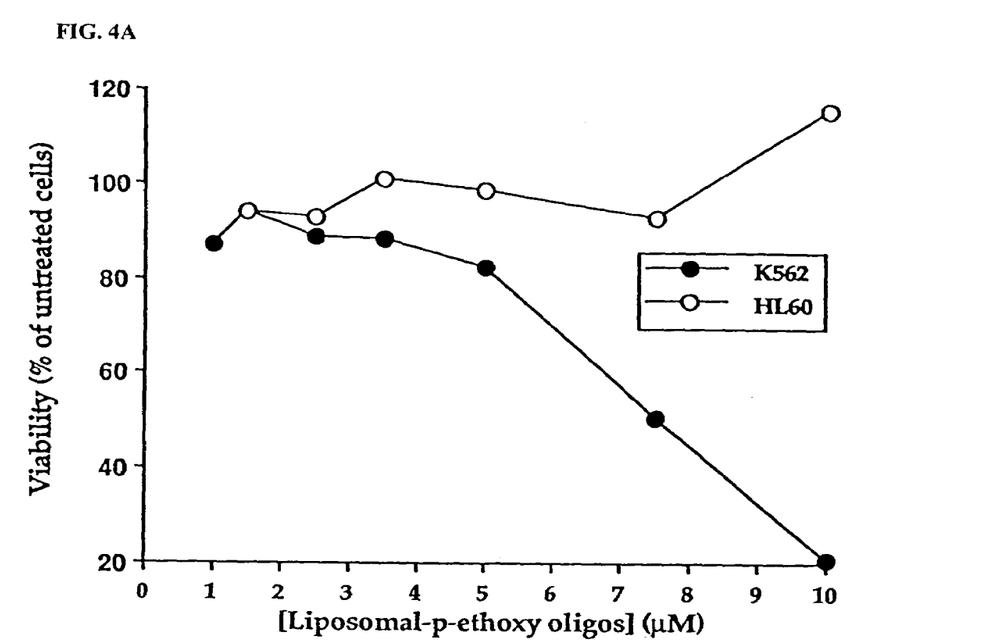
FIG. 4A shows the extent of growth inhibition that resulted when K562 and HL60 cells were incubated with liposomal-pE antisense oligos targeting against the B3/A2 breakpoint junction of Bcr-Abl mRNA.

When ALL-1 and HL60 cells were incubated with liposomal-pE antisense oligos targeted against the B1/A2 breakpoint junction of Bcr-Abl mRNA, a dose-dependent growth inhibition of ALL-1, but not HL60, cells was observed (FIG. 2A). Similarly growth inhibition was observed with BV173 and K562 cells when they were incubated with liposomal-pE antisense oligos targeting against the B2/A2 and B3/A2 breakpoint junctions of Bcr-Abl mRNA, respectively (FIGS. 3A, 4A). Under identical conditions, HL60 cells were not growth-inhibited.

Figure 2B:
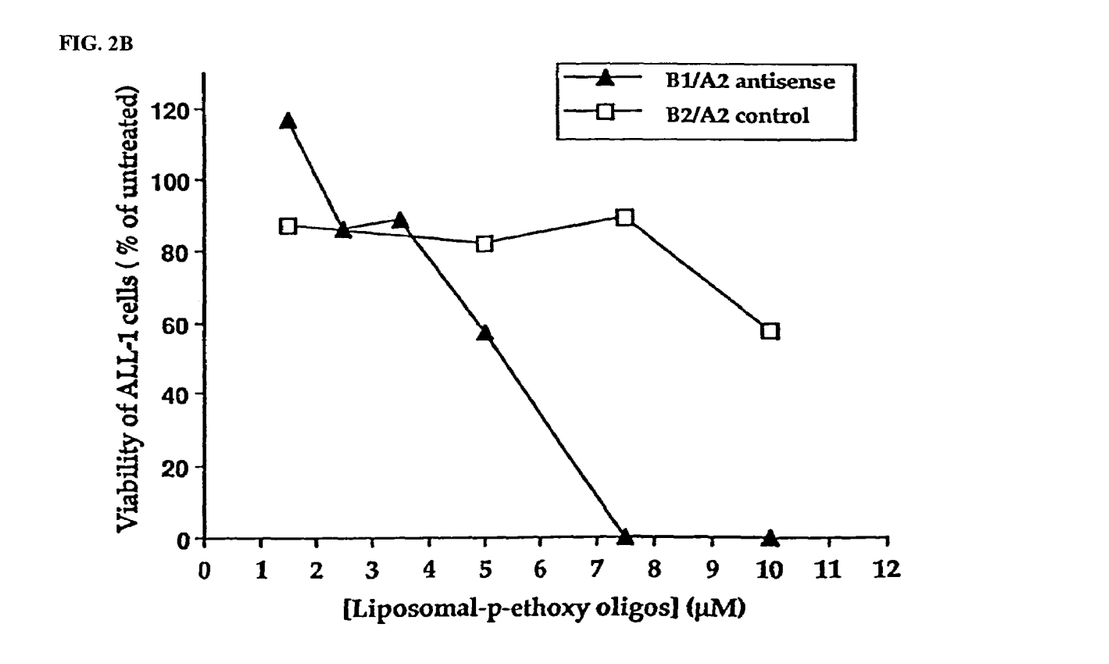
FIG. 2B shows the extent of growth inhibition that resulted when ALL-1 cells were incubated with B1/A2 liposomal-pE antisense oligos and B2/A2 liposomal-pE control oligos.
Figure 3B:
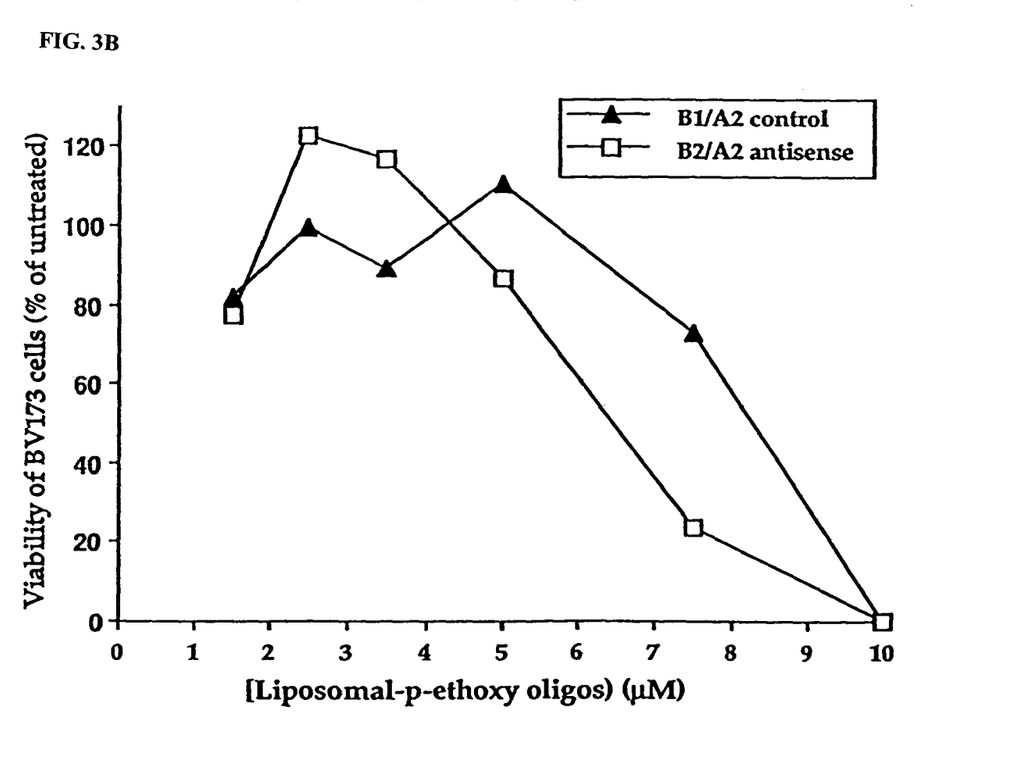
FIG. 3B shows the extent of growth inhibition that resulted when BV173 cells were incubated with liposomal-pE antisense oligos targeting against the B2/A2 breakpoint junction and with control oligos targeting against the B1/A2 breakpoint junction.
Figure 4B:
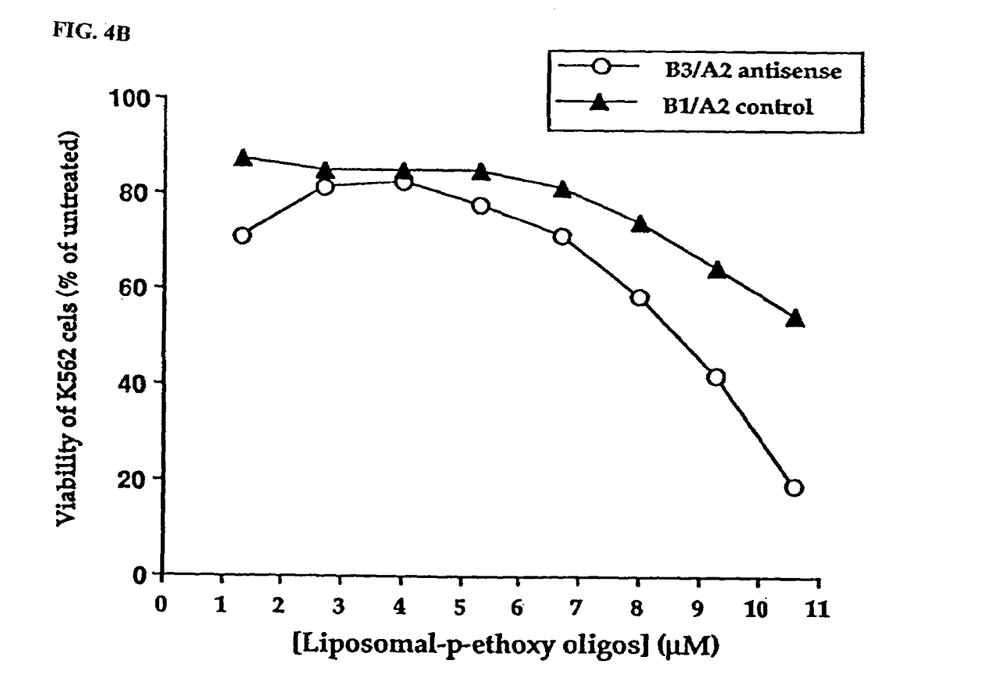
FIG. 4B shows the extent of growth inhibition that resulted when K562 cells were incubated with liposomal-pE antisense oligos targeting against the B3/A2 breakpoint junction and with control oligos targeting against the B1/A2 breakpoint junction.

To ensure that the growth inhibitory effects were sequence-dependent, the Ph chromosome-positive cell lines were incubated with antisense and control liposomal-pE oligos. When ALL-1 cells were incubated with the B1/A2 liposomal-pE antisense oligos and the B2/A2 liposomal-pE control oligos, growth inhibition was induced (FIG. 2B). However, the B1/A2 antisense oligos induced a much greater inhibitory effect. Similarly, higher inhibitory effects on BV173 and K562 cells were found with the corresponding liposomal-pE antisense oligos than with the control oligos (FIGS. 3B, 4B).

Figure 5:
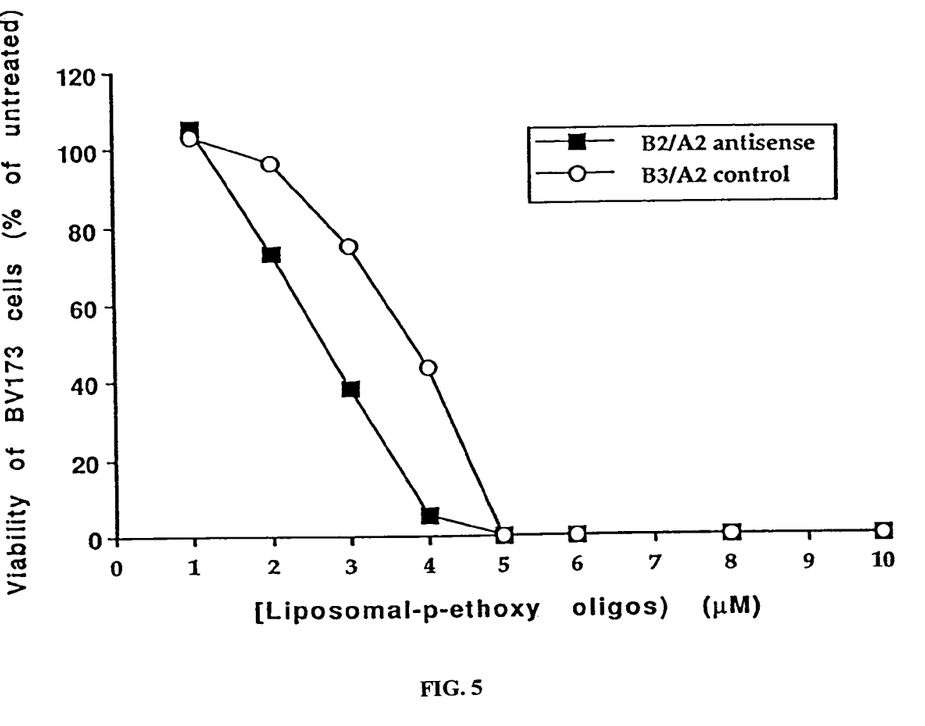
FIG. 5 shows the extent of growth inhibition that resulted when Tween 20-containing liposomal-pE oligos were incubated with BV173 cells.

We also found that by including the detergent Tween 20 in the liposomal-pE oligo mixture, the potency of the inhibitory effects of the liposomal-pE oligos was increased. We added Tween 20 at 5% (wt. of pE oligos) in the liposomal-pE oligo mixture. Then the mixture was vortexed, frozen in an acetone/dry ice bath before being lyophilized. The dried mixture was then hydrated and sonicated as stated previously. When Tween 20-containing liposomal-pE oligos were added to BV173 cells, 100% growth inhibition was observed at 5 µM (FIG. 5) whereas under the same conditions, 100% growth inhibition with normal liposomal-pE oligos (no Tween 20) was observed at 10 µM instead.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A composition comprising a p-ethoxy oligonucleotide having an antisense sequence for inhibiting the expression of a gene found in cancerous cells wherein the composition is further defined as comprising a substantially uncharged lipid component comprising neutral phospholipids.

2. The composition of claim 1, wherein the neutral phospholipids are in the form of a liposome.

3. The composition of claim 1, wherein the p-ethoxy oligonucleotide comprises the antisense sequence of SEQ. ID. NO:1.

4. The composition of claim 1, wherein the p-ethoxy oligonucleotide comprises the antisense sequence of SEQ. ID. NO:2.

5. The composition of claim 1, wherein the p-ethoxy oligonucleotide comprises the antisense sequence of SEQ. ID. NO:3.

6. The composition of claim 2, wherein the liposome consists essentially of neutral phospholipids.

* * * * *

---

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
gaagggcttc tgcgtc                                                     16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ctgaagggct tcttcc                                                     16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
gggcttttga actctgct                                                   18
```